United States Patent
O'Neil et al.

(10) Patent No.: US 11,369,490 B2
(45) Date of Patent: Jun. 28, 2022

(54) UNIVERSAL TRIAL FOR LATERAL CAGES

(71) Applicant: DEPUY SYNTHES PRODUCTS, INC., Raynham, MA (US)

(72) Inventors: Michael J O'Neil, West Barnstable, MA (US); Jonathan Bellas, Bridgewater, MA (US); Cody Cranson, Middleboro, MA (US); Sheryl Furlan, Lakeville, MA (US); Michael Toto, Canton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/421,177

(22) Filed: Jan. 31, 2017

(65) Prior Publication Data
US 2017/0135827 A1    May 18, 2017

Related U.S. Application Data

(63) Continuation of application No. 13/163,397, filed on Jun. 17, 2011, now Pat. No. 9,592,063.

(60) Provisional application No. 61/466,302, filed on Mar. 22, 2011.

(51) Int. Cl.
*A61F 2/44* (2006.01)
*A61F 2/46* (2006.01)
*A61F 2/30* (2006.01)

(52) U.S. Cl.
CPC .......... *A61F 2/4684* (2013.01); *A61F 2/4455* (2013.01); *A61F 2002/3054* (2013.01); *A61F 2002/30378* (2013.01); *A61F 2002/30406* (2013.01); *A61F 2002/443* (2013.01); *A61F 2002/4629* (2013.01); *A61F 2002/4668* (2013.01); *A61F 2310/00017* (2013.01);
(Continued)

(58) Field of Classification Search
CPC .......... A61F 2/44–447; A61F 2/4611
See application file for complete search history.

(56) References Cited

U.S. PATENT DOCUMENTS

| | | | |
|---|---|---|---|
| 4,105,034 A | 8/1978 | Shalaby |
| 4,130,639 A | 12/1978 | Shalaby |
| 4,140,678 A | 2/1979 | Shalaby |

(Continued)

FOREIGN PATENT DOCUMENTS

| | | |
|---|---|---|
| DE | 19710392 | 7/1999 |
| DE | 10357960 | 7/2005 |

(Continued)

OTHER PUBLICATIONS

Vandorpe, "Biodegradable Polyphosphazenes For Biomedical Applications"; *Handbook of Biodegradable Polymers*; 1997; pp. 161-182; Hardwood Academic Press.

(Continued)

*Primary Examiner* — Eduardo C Robert
*Assistant Examiner* — Steven J Cotroneo

(57) ABSTRACT

A method of trialing an intervertebral disc space, comprising the steps of :
a) creating the disc space,
b) inserting a trial into the disc space, the trial having i) a distal head having an upper surface and a lower surface connected by a pair of side walls, the side walls defining planes, and ii) a proximal rod,
wherein the head and rod form an obtuse angle, and
wherein the rod extends through at least one of the planes defined by the side walls of the head.

1 Claim, 12 Drawing Sheets

(52) U.S. Cl.
CPC ............... *A61F 2310/00023* (2013.01); *A61F 2310/00029* (2013.01)

(56) References Cited

U.S. PATENT DOCUMENTS

| | | |
|---|---|---|
| 4,141,087 A | 2/1979 | Shalaby |
| 4,205,399 A | 6/1980 | Shalaby |
| 4,208,511 A | 6/1980 | Shalaby |
| 4,538,612 A | 9/1985 | Patrick, Jr. |
| 4,834,757 A | 5/1989 | Brantigan |
| 4,863,476 A | 9/1989 | Shepperd |
| 4,995,200 A | 2/1991 | Eberhart |
| 5,006,121 A | 4/1991 | Hafeli |
| 5,019,082 A | 5/1991 | Frey |
| 5,123,926 A | 6/1992 | Piahsrodi |
| 5,133,719 A | 7/1992 | Winston |
| 5,163,939 A | 11/1992 | Winston |
| 5,169,402 A | 12/1992 | Elloy |
| 5,171,278 A | 12/1992 | Pisharodi |
| 5,217,475 A | 6/1993 | Kuber |
| 5,250,061 A | 10/1993 | Michelson |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,454,815 A | 10/1995 | Geisser |
| 5,454,827 A | 10/1995 | Aust |
| 5,464,929 A | 11/1995 | Bezwada |
| 5,522,899 A | 6/1996 | Michelson |
| 5,540,693 A | 7/1996 | Fisher |
| 5,554,191 A | 9/1996 | Lahille |
| 5,595,751 A | 1/1997 | Bezwada |
| 5,597,579 A | 1/1997 | Bezwada |
| 5,601,561 A | 2/1997 | Terry |
| 5,607,687 A | 3/1997 | Bezwada |
| 5,609,635 A * | 3/1997 | Michelson ............... A61F 2/442 623/17.16 |
| 5,618,552 A | 4/1997 | Bezwada |
| 5,620,698 A | 4/1997 | Bezwada |
| 5,645,850 A | 7/1997 | Bezwada |
| 5,648,088 A | 7/1997 | Bezwada |
| 5,658,335 A | 8/1997 | Allen |
| 5,665,122 A | 9/1997 | Kambin |
| 5,693,100 A | 12/1997 | Pisharodi |
| 5,698,213 A | 12/1997 | Jamiolkowski |
| 5,700,583 A | 12/1997 | Jamiolkowski |
| 5,725,531 A | 3/1998 | Shapiro |
| 5,857,995 A | 1/1999 | Thomas |
| 5,859,150 A | 1/1999 | Jamiolkowski |
| 5,865,848 A | 2/1999 | Baker |
| 5,916,228 A | 6/1999 | Ripich |
| 5,916,267 A | 6/1999 | Tienboon |
| 5,925,056 A | 7/1999 | Thomas |
| 5,976,187 A | 11/1999 | Richelsoph |
| 5,980,522 A | 11/1999 | Koros |
| 6,039,761 A | 3/2000 | Li |
| 6,045,579 A | 4/2000 | Hochshuler et al. |
| 6,053,922 A | 4/2000 | Krause |
| 6,056,763 A | 5/2000 | Parsons |
| 6,066,175 A | 5/2000 | Henderson |
| 6,080,158 A | 6/2000 | Lin |
| 6,106,557 A | 8/2000 | Robioneck |
| 6,120,508 A | 9/2000 | Grunig |
| 6,126,689 A | 10/2000 | Brett |
| 6,139,558 A | 10/2000 | Wagner |
| 6,176,882 B1 | 1/2001 | Biedermann |
| 6,241,733 B1 | 6/2001 | Nicholson |
| 6,251,140 B1 | 6/2001 | Marino |
| 6,258,093 B1 | 7/2001 | Edwards |
| 6,296,644 B1 | 10/2001 | Saurat |
| D450,676 S | 11/2001 | Huttner |
| 6,332,894 B1 | 12/2001 | Stalcup et al. |
| 6,342,074 B1 | 1/2002 | Simpson |
| 6,387,130 B1 | 5/2002 | Stone |
| 6,398,793 B1 | 6/2002 | McGuire |
| 6,409,766 B1 | 6/2002 | Brett |
| 6,413,278 B1 | 7/2002 | Marchosky |
| 6,436,101 B1 | 8/2002 | Hamada |
| 6,447,518 B1 | 9/2002 | Krause |
| 6,579,318 B2 | 6/2003 | Ogilvie |
| 6,595,998 B2 | 7/2003 | Johnson et al. |
| 6,610,066 B2 | 8/2003 | Dinger |
| 6,635,060 B2 | 10/2003 | Hanson |
| RE38,335 E | 11/2003 | Aust |
| 6,641,582 B1 | 11/2003 | Hanson |
| 6,660,004 B2 | 12/2003 | Barker |
| 6,733,535 B2 | 5/2004 | Michelson |
| 6,746,451 B2 | 6/2004 | Middleton et al. |
| 6,755,837 B2 | 6/2004 | Ebner |
| 6,758,847 B2 | 7/2004 | Maguire |
| 6,764,491 B2 | 7/2004 | Frey |
| 6,835,208 B2 | 12/2004 | Marchosky |
| 6,840,941 B2 | 1/2005 | Rogers |
| 6,852,127 B2 | 2/2005 | Ogilvie |
| 6,878,167 B2 | 4/2005 | Ferree |
| 6,949,108 B2 | 9/2005 | Holmes |
| 6,966,912 B2 | 11/2005 | Michelson |
| 7,018,415 B1 | 3/2006 | McKay |
| 7,060,073 B2 | 6/2006 | Frey |
| 7,063,725 B2 | 6/2006 | Foley |
| 7,070,598 B2 | 7/2006 | Lim |
| 7,087,053 B2 | 8/2006 | Vanney |
| 7,087,055 B2 | 8/2006 | Lim |
| 7,089,063 B2 | 8/2006 | Lesh |
| 7,125,424 B2 | 10/2006 | Banick |
| 7,226,482 B2 | 6/2007 | Messerli |
| 7,326,248 B2 | 2/2008 | Michelson |
| 7,351,262 B2 | 4/2008 | Bindseil |
| 7,406,775 B2 * | 8/2008 | Funk ............... A61F 2/4405 33/512 |
| 7,470,273 B2 | 12/2008 | Dougherty-Shah |
| 7,491,237 B2 | 2/2009 | Randall |
| 7,503,920 B2 | 3/2009 | Siegal |
| 7,572,279 B2 | 8/2009 | Jackson |
| 7,575,580 B2 | 8/2009 | Lim |
| 7,578,820 B2 | 8/2009 | Moore |
| 7,601,173 B2 | 10/2009 | Messerli |
| 7,618,458 B2 | 11/2009 | Biedermann |
| 7,625,377 B2 | 12/2009 | Veldhuizen |
| 7,625,394 B2 | 12/2009 | Molz, IV |
| 7,655,010 B2 | 2/2010 | Serhan et al. |
| 7,666,186 B2 | 2/2010 | Harp |
| 7,666,226 B2 | 2/2010 | Schaller |
| 7,670,374 B2 | 3/2010 | Schaller |
| 7,674,265 B2 | 3/2010 | Smith |
| 7,682,400 B2 | 3/2010 | Zwirkoski |
| 7,703,727 B2 | 4/2010 | Selness |
| 7,704,280 B2 | 4/2010 | Lechmann |
| 7,731,751 B2 | 6/2010 | Butler |
| 7,763,028 B2 | 7/2010 | Lim |
| 7,763,038 B2 | 7/2010 | O'Brien |
| 7,771,473 B2 | 8/2010 | Thramann |
| 7,785,368 B2 | 8/2010 | Schaller |
| 7,799,081 B2 | 9/2010 | McKinley |
| 7,803,161 B2 | 9/2010 | Foley |
| 7,828,849 B2 | 11/2010 | Lim |
| 7,837,734 B2 | 11/2010 | Zucherman |
| 7,850,733 B2 | 12/2010 | Baynham |
| 7,918,874 B2 | 4/2011 | Siegal |
| 7,922,719 B2 | 4/2011 | Ralph |
| 7,938,857 B2 | 5/2011 | Garcia-Bengochea |
| 7,942,903 B2 | 5/2011 | Moskowitz |
| 7,963,967 B1 | 6/2011 | Woods |
| 8,007,535 B2 | 8/2011 | Hudgins |
| 8,012,212 B2 | 9/2011 | Link |
| 8,025,697 B2 | 9/2011 | McClellan, III |
| 8,034,110 B2 | 10/2011 | Garner et al. |
| 8,038,703 B2 | 10/2011 | Dobak, III |
| 8,043,293 B2 * | 10/2011 | Warnick ............... A61F 2/4465 606/249 |
| 8,057,544 B2 | 11/2011 | Schaller |
| 8,105,382 B2 | 1/2012 | Olmos |
| 8,128,700 B2 | 3/2012 | Delurio |
| 8,206,423 B2 | 6/2012 | Siegal |

(56) References Cited

U.S. PATENT DOCUMENTS

| | | | |
|---|---|---|---|
| 8,216,317 B2* | 7/2012 | Thibodeau | A61F 2/4455 606/279 |
| 8,241,364 B2 | 8/2012 | Hansell | |
| 8,262,666 B2 | 9/2012 | Baynham | |
| 8,267,939 B2 | 9/2012 | Cipoletti | |
| 8,343,193 B2 | 1/2013 | Johnson et al. | |
| 8,343,222 B2 | 1/2013 | Cope | |
| 8,366,777 B2 | 2/2013 | Matthis | |
| 8,382,842 B2 | 2/2013 | Greenhalgh et al. | |
| 8,403,990 B2 | 3/2013 | Dryer et al. | |
| 8,454,617 B2 | 6/2013 | Schaller et al. | |
| 8,470,043 B2 | 6/2013 | Schaller | |
| 8,579,981 B2 | 11/2013 | Lim | |
| 8,628,577 B1 | 1/2014 | Jimenez | |
| 8,663,331 B2 | 3/2014 | McClellan, III | |
| 8,740,954 B2 | 6/2014 | Georgy | |
| 8,758,349 B2 | 6/2014 | Germain et al. | |
| 8,845,733 B2 | 9/2014 | O'Neil | |
| 8,845,734 B2 | 9/2014 | O'Neil et al. | |
| 8,920,506 B2 | 12/2014 | McGuckin, Jr. | |
| 8,926,704 B2 | 1/2015 | Glerum et al. | |
| 8,940,050 B2 | 1/2015 | Laurence | |
| 8,961,609 B2 | 2/2015 | Schaller | |
| 8,968,408 B2 | 3/2015 | Schaller et al. | |
| 9,101,488 B2 | 8/2015 | Malandain | |
| 9,101,491 B2 | 8/2015 | Rodgers | |
| 9,101,492 B2 | 8/2015 | Mangione | |
| 9,282,979 B2 | 3/2016 | O'Neil | |
| 9,801,639 B2 | 10/2017 | O'Neil | |
| 9,801,640 B2 | 10/2017 | O'Neil | |
| 10,405,989 B2 | 9/2019 | O'Neil | |
| 2002/0138078 A1 | 9/2002 | Chappuis | |
| 2002/0143399 A1 | 10/2002 | Sutcliffe | |
| 2002/0165550 A1 | 11/2002 | Frey | |
| 2002/0183758 A1 | 12/2002 | Middleton | |
| 2003/0028251 A1 | 2/2003 | Matthews | |
| 2003/0033017 A1* | 2/2003 | Lotz | A61F 2/441 623/17.16 |
| 2003/0135275 A1 | 7/2003 | Garcia | |
| 2003/0139812 A1 | 7/2003 | Garcia et al. | |
| 2003/0191531 A1 | 10/2003 | Berry | |
| 2004/0002761 A1 | 1/2004 | Rogers et al. | |
| 2004/0030387 A1 | 2/2004 | Landry | |
| 2004/0059337 A1 | 3/2004 | Hanson | |
| 2004/0068269 A1* | 4/2004 | Bonati | A61B 17/8891 606/104 |
| 2004/0068318 A1 | 4/2004 | Coates et al. | |
| 2004/0078079 A1* | 4/2004 | Foley | A61B 17/025 623/17.11 |
| 2004/0083000 A1 | 4/2004 | Keller | |
| 2004/0087947 A1 | 5/2004 | Lim et al. | |
| 2004/0102784 A1 | 5/2004 | Pasquet | |
| 2004/0102846 A1 | 5/2004 | Keller | |
| 2004/0127990 A1 | 7/2004 | Bartish | |
| 2004/0147129 A1 | 7/2004 | Rolfson | |
| 2004/0220668 A1 | 11/2004 | Eisermann | |
| 2005/0038431 A1 | 2/2005 | Bartish | |
| 2005/0096745 A1 | 5/2005 | Andre | |
| 2005/0119752 A1 | 6/2005 | Williams et al. | |
| 2005/0149034 A1 | 7/2005 | Assell | |
| 2005/0165420 A1 | 7/2005 | Cha | |
| 2005/0165484 A1 | 7/2005 | Ferree | |
| 2005/0171541 A1 | 8/2005 | Boehm | |
| 2005/0177173 A1 | 8/2005 | Aebi | |
| 2005/0240193 A1 | 10/2005 | Layne | |
| 2005/0261683 A1 | 11/2005 | Veldhuizen | |
| 2005/0267463 A1 | 12/2005 | Vanney | |
| 2006/0036244 A1* | 2/2006 | Spitler | A61B 5/103 74/1 R |
| 2006/0276902 A1 | 2/2006 | Zipnick | |
| 2006/0058807 A1 | 3/2006 | Landry | |
| 2006/0064101 A1 | 3/2006 | Arramon | |
| 2006/0064102 A1 | 3/2006 | Ebner | |
| 2006/0069436 A1* | 3/2006 | Sutton | A61F 2/4684 623/17.13 |
| 2006/0074429 A1 | 4/2006 | Ralph | |
| 2006/0100622 A1 | 5/2006 | Jackson | |
| 2006/0111715 A1 | 5/2006 | Jackson | |
| 2006/0111728 A1 | 5/2006 | Abdou | |
| 2006/0122701 A1 | 6/2006 | Kiester | |
| 2006/0129244 A1 | 6/2006 | Ensign | |
| 2006/0142858 A1 | 6/2006 | Colleran | |
| 2006/0167547 A1 | 7/2006 | Suddaby | |
| 2006/0189999 A1 | 8/2006 | Zwirkoski | |
| 2006/0212118 A1 | 9/2006 | Abernathie | |
| 2006/0229627 A1 | 10/2006 | Hunt | |
| 2006/0229724 A1 | 10/2006 | Lechmann | |
| 2006/0235426 A1 | 10/2006 | Lim | |
| 2006/0253120 A1* | 11/2006 | Anderson | A61B 17/808 606/86 R |
| 2006/0254784 A1* | 11/2006 | Hartmann | A61B 17/7005 172/789 |
| 2006/0265077 A1 | 11/2006 | Zwirkoski | |
| 2006/0293753 A1 | 12/2006 | Thramann | |
| 2007/0055264 A1 | 3/2007 | Parmigiani | |
| 2007/0055272 A1 | 3/2007 | Schaller | |
| 2007/0067035 A1 | 3/2007 | Falahee | |
| 2007/0093897 A1 | 4/2007 | Gerbec | |
| 2007/0093901 A1 | 4/2007 | Grotz et al. | |
| 2007/0142843 A1 | 6/2007 | Dye | |
| 2007/0162132 A1 | 7/2007 | Messerli | |
| 2007/0162138 A1* | 7/2007 | Heinz | A61F 2/4611 623/17.16 |
| 2007/0213737 A1* | 9/2007 | Schermerhorn | A61F 2/4465 606/86 R |
| 2007/0213826 A1 | 9/2007 | Smith | |
| 2007/0225726 A1* | 9/2007 | Dye | A61F 2/4465 606/99 |
| 2007/0225815 A1 | 9/2007 | Keith | |
| 2007/0233130 A1 | 10/2007 | Suddaby | |
| 2007/0250167 A1 | 10/2007 | Bray et al. | |
| 2007/0260314 A1 | 11/2007 | Biyani | |
| 2007/0270957 A1 | 11/2007 | Heinz | |
| 2007/0270968 A1 | 11/2007 | Baynham | |
| 2008/0027544 A1* | 1/2008 | Melkent | A61F 2/442 623/17.11 |
| 2008/0027550 A1 | 1/2008 | Link | |
| 2008/0045966 A1 | 2/2008 | Buttermann | |
| 2008/0051890 A1 | 2/2008 | Waugh | |
| 2008/0058933 A1 | 3/2008 | Garner | |
| 2008/0065082 A1* | 3/2008 | Chang | A61B 17/1659 606/85 |
| 2008/0077150 A1 | 3/2008 | Nguyen | |
| 2008/0077241 A1 | 3/2008 | Nguyen | |
| 2008/0082173 A1 | 4/2008 | Delurio | |
| 2008/0091211 A1 | 4/2008 | Gately | |
| 2008/0097454 A1 | 4/2008 | DeRidder | |
| 2008/0108990 A1 | 5/2008 | Mitchell | |
| 2008/0119935 A1 | 5/2008 | Alvarez | |
| 2008/0125865 A1 | 5/2008 | Abdelgany | |
| 2008/0133012 A1 | 6/2008 | McGuckin | |
| 2008/0140085 A1* | 6/2008 | Gately | A61F 2/4465 606/99 |
| 2008/0147129 A1 | 6/2008 | Biedermann et al. | |
| 2008/0154379 A1 | 6/2008 | Steiner | |
| 2008/0172128 A1 | 7/2008 | Perez-Cruet et al. | |
| 2008/0208255 A1 | 8/2008 | Siegal | |
| 2008/0221586 A1 | 9/2008 | Garcia-Bengochea | |
| 2008/0221687 A1 | 9/2008 | Viker | |
| 2008/0234732 A1 | 9/2008 | Landry | |
| 2008/0234733 A1 | 9/2008 | Scrantz | |
| 2008/0243126 A1 | 10/2008 | Gutierrez | |
| 2008/0243255 A1 | 10/2008 | Butler | |
| 2008/0249628 A1 | 10/2008 | Altarac | |
| 2008/0255563 A1 | 10/2008 | Farr | |
| 2008/0255574 A1 | 10/2008 | Dye | |
| 2008/0269904 A1 | 10/2008 | Voorhies | |
| 2008/0312743 A1 | 12/2008 | Vila | |
| 2009/0030423 A1 | 1/2009 | Puno | |
| 2009/0054898 A1 | 2/2009 | Gleason | |
| 2009/0054911 A1 | 2/2009 | Mueller | |

(56) References Cited

U.S. PATENT DOCUMENTS

| | | |
|---|---|---|
| 2009/0062807 A1 | 3/2009 | Song |
| 2009/0076607 A1* | 3/2009 | Aalsma .............. A61B 17/8852 623/17.16 |
| 2009/0088789 A1 | 4/2009 | O'Neil |
| 2009/0112217 A1 | 4/2009 | Hester |
| 2009/0143859 A1 | 6/2009 | McClellan, III |
| 2009/0164016 A1 | 6/2009 | Georgy |
| 2009/0182431 A1 | 7/2009 | Butler |
| 2009/0192616 A1 | 7/2009 | Zielinski |
| 2009/0216234 A1 | 8/2009 | Farr |
| 2009/0221967 A1 | 9/2009 | Thommen |
| 2009/0234364 A1 | 9/2009 | Crook |
| 2009/0240335 A1 | 9/2009 | Arcenio |
| 2009/0276049 A1 | 11/2009 | Weiland |
| 2009/0299479 A1* | 12/2009 | Jones ..................... A61F 2/4465 623/17.16 |
| 2010/0016968 A1 | 1/2010 | Moore |
| 2010/0030217 A1 | 2/2010 | Mitusina |
| 2010/0076502 A1 | 3/2010 | Guyer |
| 2010/0094422 A1 | 4/2010 | Hansell |
| 2010/0100098 A1 | 4/2010 | Norton |
| 2010/0100183 A1 | 4/2010 | Prewett |
| 2010/0125334 A1 | 5/2010 | Krueger |
| 2010/0161060 A1 | 6/2010 | Schaller |
| 2010/0174321 A1 | 7/2010 | Schaller |
| 2010/0185290 A1 | 7/2010 | Compton |
| 2010/0191241 A1 | 7/2010 | McCormack |
| 2010/0198263 A1 | 8/2010 | Siegal |
| 2010/0211076 A1 | 8/2010 | Germain |
| 2010/0211107 A1 | 8/2010 | Muhanna |
| 2010/0217269 A1 | 8/2010 | Landes |
| 2010/0234849 A1 | 9/2010 | Bouadi |
| 2010/0249935 A1 | 9/2010 | Slivka |
| 2010/0256768 A1 | 10/2010 | Lim |
| 2010/0274358 A1 | 10/2010 | Mueller et al. |
| 2010/0280619 A1 | 11/2010 | Yuan |
| 2010/0305700 A1 | 12/2010 | Ben-Arye |
| 2010/0305704 A1 | 12/2010 | Messerli |
| 2010/0331845 A1 | 12/2010 | Foley |
| 2011/0004216 A1 | 1/2011 | Amendola |
| 2011/0009970 A1 | 1/2011 | Puno |
| 2011/0029083 A1 | 2/2011 | Hynes |
| 2011/0029085 A1 | 2/2011 | Hynes |
| 2011/0035011 A1 | 2/2011 | Cain |
| 2011/0106260 A1 | 5/2011 | Laurence |
| 2011/0112586 A1 | 5/2011 | Guyer |
| 2011/0125266 A1 | 5/2011 | Rodgers |
| 2011/0190891 A1 | 8/2011 | Suh et al. |
| 2011/0276142 A1 | 11/2011 | Niemiec |
| 2011/0282459 A1 | 11/2011 | McClellan, III |
| 2011/0301712 A1 | 12/2011 | Palmatier et al. |
| 2011/0319898 A1 | 12/2011 | O'Neil |
| 2011/0319899 A1 | 12/2011 | O'Neil |
| 2011/0319998 A1 | 12/2011 | O'Neil |
| 2011/0319999 A1 | 12/2011 | O'Neil |
| 2011/0320000 A1 | 12/2011 | O'Neil |
| 2012/0010715 A1 | 1/2012 | Spann |
| 2012/0035730 A1 | 2/2012 | Spann |
| 2012/0165943 A1 | 6/2012 | Mangione |
| 2012/0209383 A1 | 8/2012 | Tsuang |
| 2012/0277877 A1 | 11/2012 | Smith |
| 2012/0310352 A1 | 12/2012 | DiMauro et al. |
| 2013/0006362 A1 | 1/2013 | Biedermann |
| 2013/0023937 A1 | 1/2013 | Biedermann |
| 2013/0035762 A1 | 2/2013 | Siegal |
| 2013/0079790 A1 | 3/2013 | Stein |
| 2013/0109925 A1 | 5/2013 | Horton |
| 2013/0110239 A1 | 5/2013 | Siegal et al. |
| 2013/0116791 A1 | 5/2013 | Theofilos |
| 2013/0138214 A1 | 5/2013 | Greenhalgh |
| 2013/0150906 A1 | 6/2013 | Kerboul |
| 2013/0173004 A1 | 7/2013 | Greenhalgh |
| 2013/0190875 A1 | 7/2013 | Shulock |
| 2013/0238006 A1 | 9/2013 | O'Neil |
| 2013/0268077 A1 | 10/2013 | You |
| 2013/0310937 A1 | 11/2013 | Pimenta |
| 2014/0025170 A1 | 1/2014 | Lim |
| 2014/0039626 A1 | 2/2014 | Mitchell |
| 2014/0052259 A1 | 2/2014 | Garner et al. |
| 2014/0058512 A1 | 2/2014 | Petersheim |
| 2014/0058513 A1 | 2/2014 | Gahman |
| 2014/0172103 A1 | 6/2014 | O'Neil |
| 2014/0172105 A1 | 6/2014 | Frasier |
| 2015/0032212 A1 | 1/2015 | O'Neil |
| 2015/0094812 A1 | 4/2015 | Cain |
| 2015/0196400 A1 | 7/2015 | Dace |
| 2016/0038306 A1 | 2/2016 | O'Neil |
| 2017/0128231 A1 | 5/2017 | O'Neil |
| 2018/0028200 A1 | 2/2018 | O'Neil |
| 2018/0036141 A1 | 2/2018 | O'Neil |

FOREIGN PATENT DOCUMENTS

| | | |
|---|---|---|
| EP | 0509084 | 10/1992 |
| EP | 609084 | 9/1997 |
| EP | 1283026 | 9/2003 |
| EP | 1405602 | 4/2004 |
| EP | 1308132 | 12/2006 |
| EP | 1829486 | 9/2007 |
| FR | 2874814 | 3/2006 |
| FR | 2948277 | 1/2011 |
| WO | 199207594 | 5/1992 |
| WO | WO 1992014423 | 9/1992 |
| WO | WO 1998034568 | 8/1998 |
| WO | WO 1999060956 | 12/1999 |
| WO | WO 1999063914 | 12/1999 |
| WO | WO 2000024343 | 5/2000 |
| WO | WO 200074605 | 12/2000 |
| WO | WO 01/95838 | 12/2001 |
| WO | WO 2002003870 | 1/2002 |
| WO | WO 2003003951 | 1/2003 |
| WO | WO 2004080316 | 9/2004 |
| WO | WO 2004069033 | 1/2005 |
| WO | 2005094297 | 10/2005 |
| WO | WO 2005094297 | 10/2005 |
| WO | WO 2004080316 | 12/2005 |
| WO | WO 2006118944 | 11/2006 |
| WO | WO 2006044920 | 12/2006 |
| WO | WO 2007048012 | 4/2007 |
| WO | WO 2008005627 | 1/2008 |
| WO | WO 2006072941 | 7/2008 |
| WO | WO 2010011348 | 1/2010 |
| WO | WO 2010075555 | 10/2010 |
| WO | WO 2010121002 | 12/2010 |
| WO | WO 2011013047 | 4/2011 |
| WO | WO 2011060087 | 5/2011 |
| WO | WO 2012129197 | 9/2012 |
| WO | WO 2013149611 | 10/2013 |
| WO | WO 2012027490 | 3/2014 |
| WO | WO 2012103254 | 4/2014 |

OTHER PUBLICATIONS

Allcock, "Polyphosphazenes"; *The Encyclopedia of Polymer Science*; 1988; pp. 31-41; vol. 13; Wiley Intersciences, John Wiley & Sons.

Cohn, "Polymer Preprints"; *Journal of Biomaterials Research*; 1989; p. 498; Biomaterials Research Labortatory, Casali Institute of Applied Chemistry, Israel.

Cohn, "Biodegradable PEO/PLA Block Copolymers"; *Journal of Biomedical Materials Research*; 1988; pp. 993-1009; vol. 22; John Wiley & Sons, Inc.

Heller, "Poly (Otrho Esters)"; *Handbook of Biodegradable Polymers*; edited by Domb; et al; Hardwood Academic Press; 1997; pp. 99-118.

Kemnitzer, "Degradable Polymers Derived From The Amino Acid L-Tyrosine"; 1997; pp. 251-272; edited by Domb, et. al., Hardwood Academic Press.

Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.

(56) References Cited

OTHER PUBLICATIONS

U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.

* cited by examiner

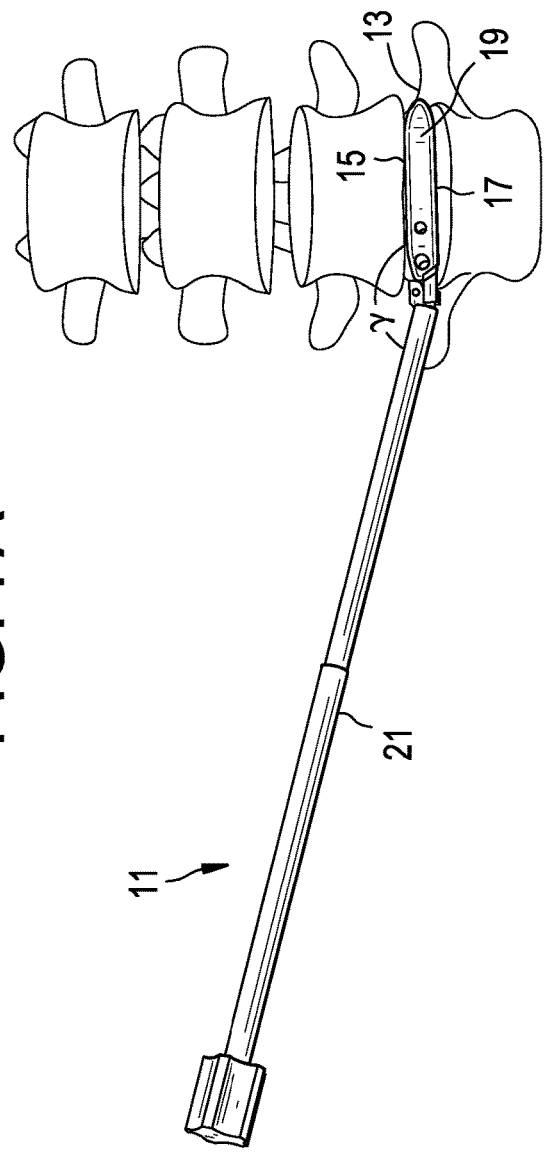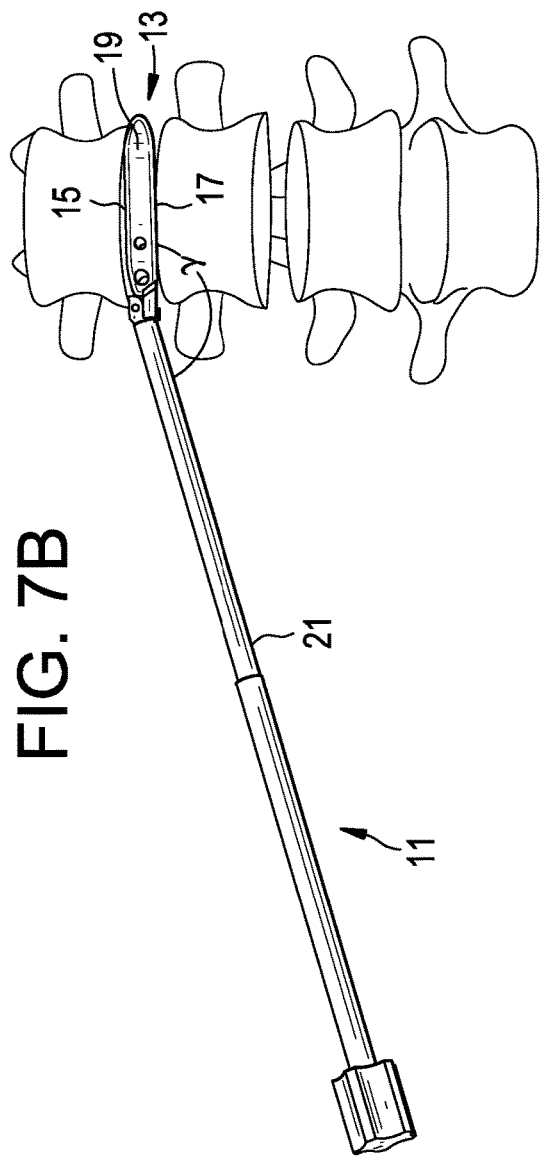

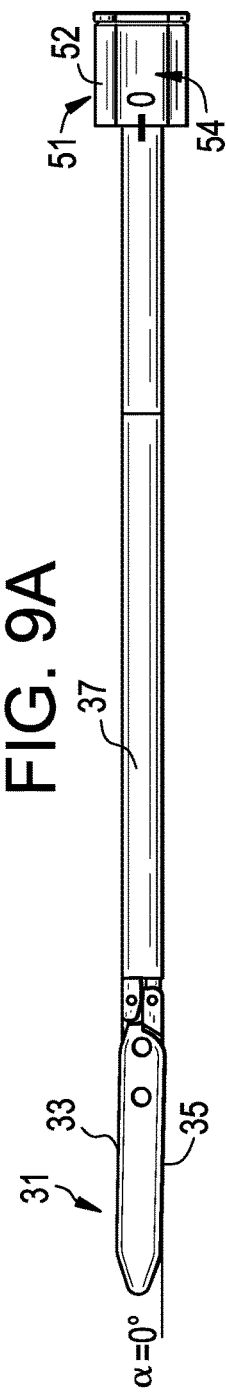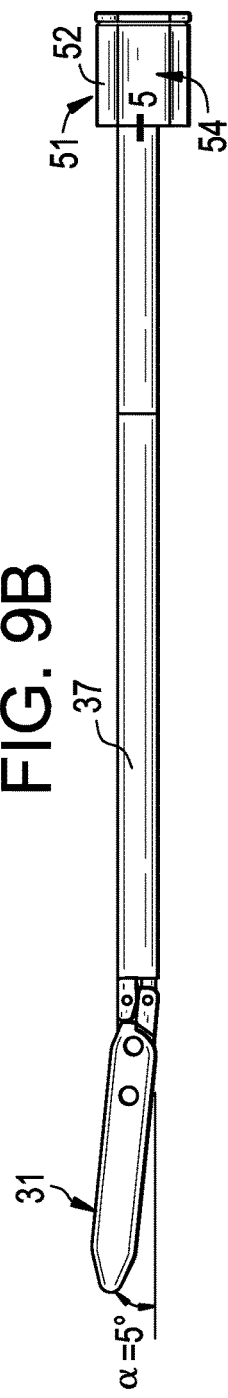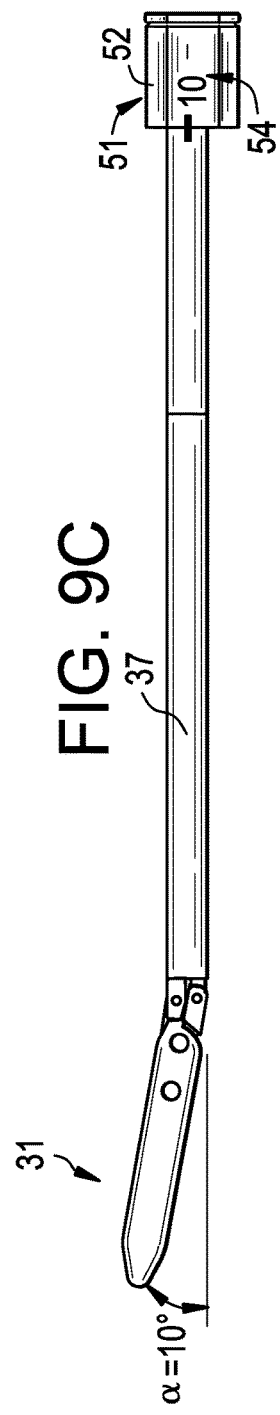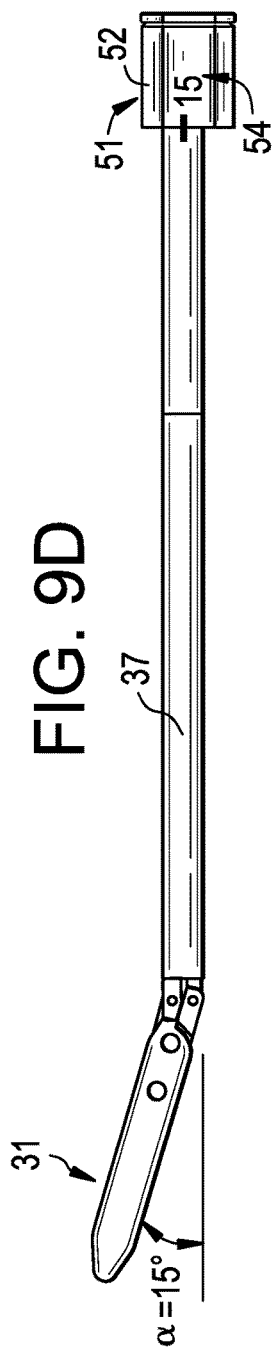

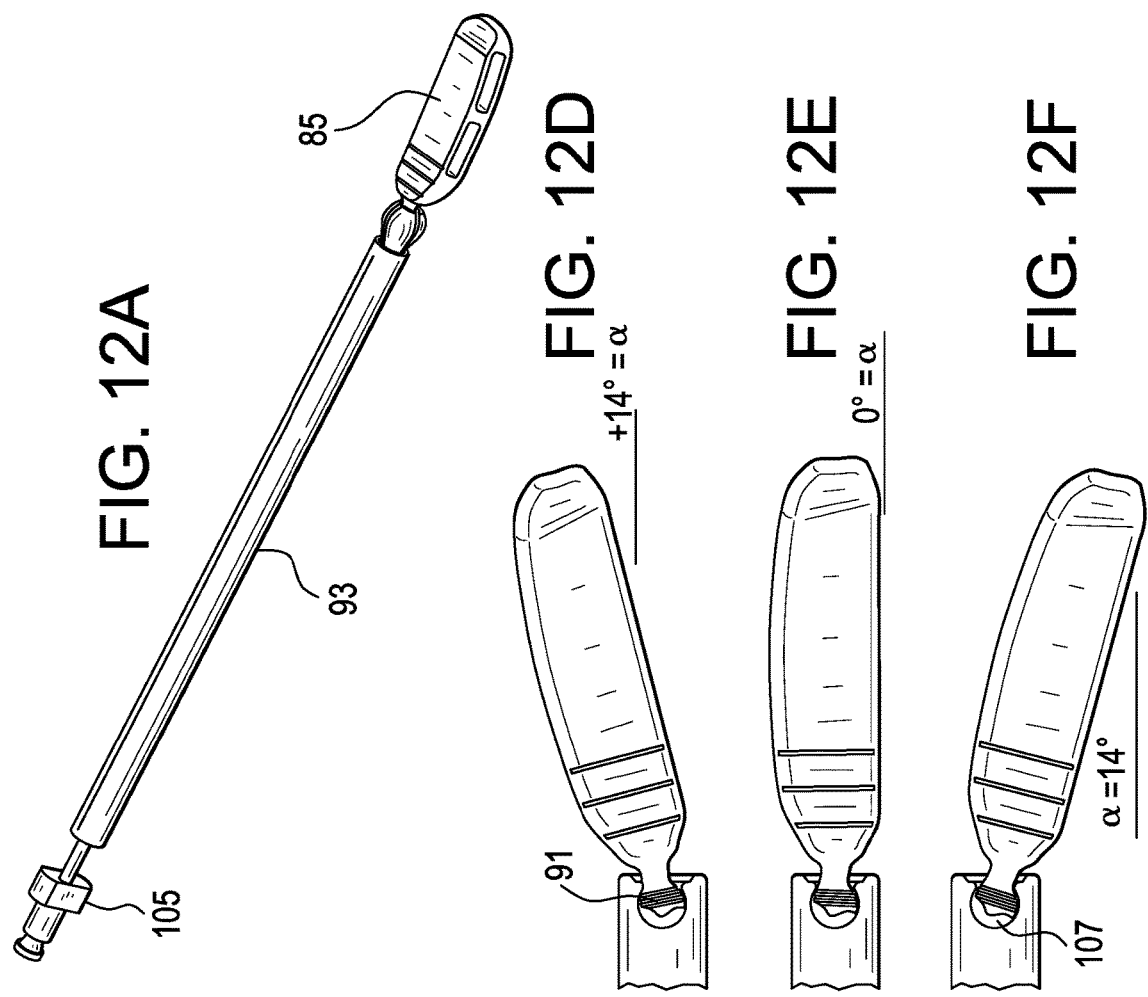

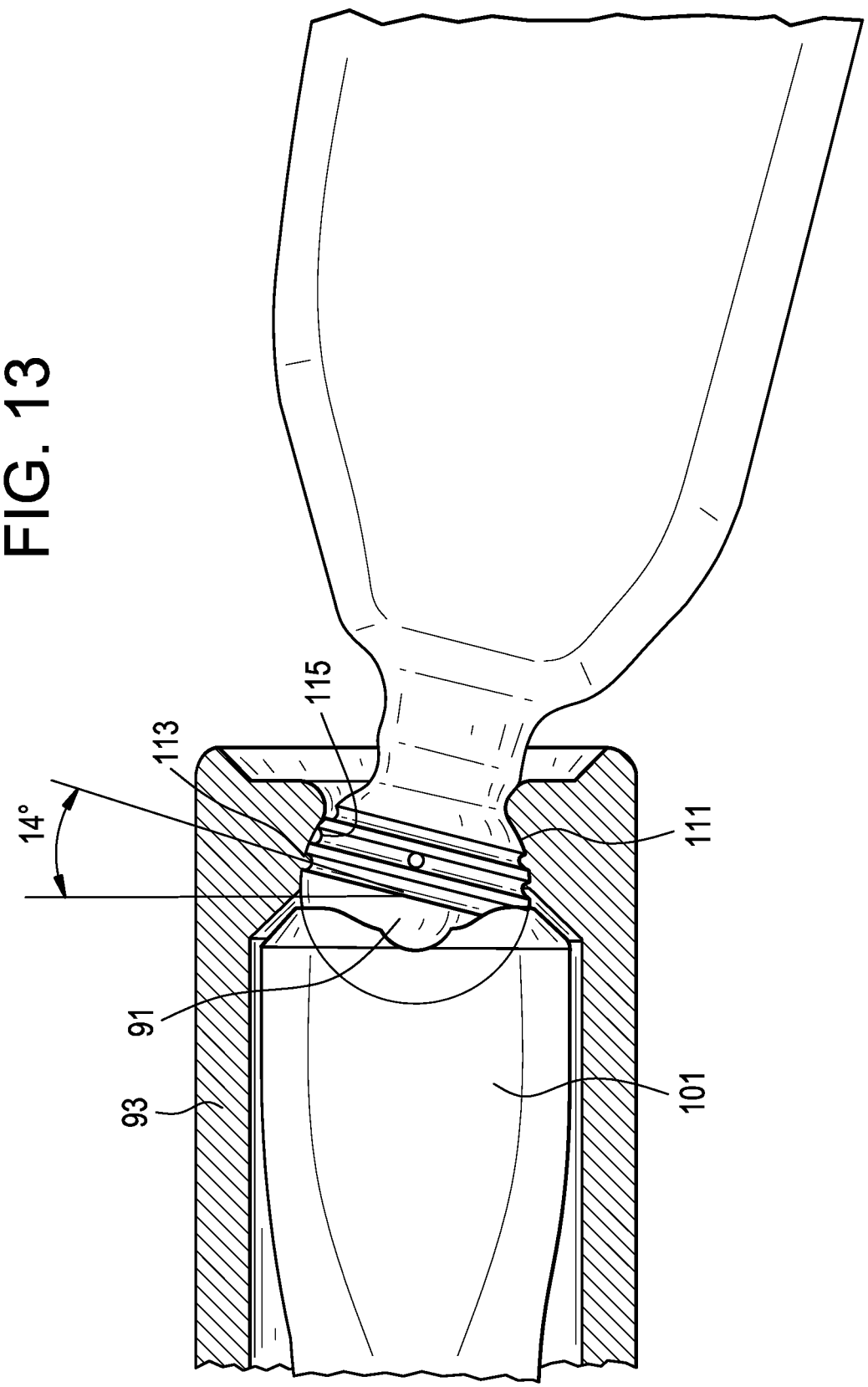

UNIVERSAL TRIAL FOR LATERAL CAGES

CONTINUING DATA

This application is a continuation of U.S. Ser. No. 13/163,397, filed Jun. 17, 2011, entitled "Universal Trial for Lateral Cages" (DEP6390USNP), which claims priority from provisional application U.S. Ser. No. 61/466,302, filed Mar. 22, 2011, entitled Universal Trial for Lateral Cages, the specification of which is incorporated by reference in its entirety.

BACKGROUND OF THE INVENTION

In spine surgery, lateral access approaches are increasingly used to deliver interbody fusion cages to the lumbar spine. These lateral approaches are gaining in popularity because they minimize posterior and/or anterior tissue damage, as well as reduce operating room time and associated blood loss, and infection risk. Conventional lateral approaches include the following: Direct Lateral (transpsoas entry parallel cranially and caudally with the disc space, or retract the psoas); Anterior-Lateral (anterior to the psoas parallel to the disc space); and Superior/Inferior Lateral (non-parallel lateral access to the disc space). See instruments A-C in FIGS. 1-5.

The use of multiple lateral approaches has required the development of a trialing system for each approach, thus increasing the number of surgical instruments and overall procedure cost. Specifically-angled trials limit the surgical approaches to the single specific angle of the trial.

Currently, no conventional trial system allows for determination of the angle of the implanted trial following its satisfactory placement and imaging.

US Patent Publication No. 2008-0077241 (Nguyen) discloses a method of preparing a pair of adjacent vertebral endplates, involving a surgical instrument having a pivoting distal removable insert, a proximal handle portion, a body portion, and a linkage member positioned between the insert and the proximal handle portion, the insert having a first angular position relative to the body. A leading end of the insert may be placed in a first position between two adjacent vertebral endplates and moved to a second position between the adjacent vertebral endplates by impacting the proximal end portion of the surgical instrument. The insert may be pivoted to a second angular position relative to the body portion by rotating the handle about the body portion and may lock the second angular position of the distal insert. The insert may be moved to a third position between the adjacent vertebral endplates by impacting the proximal end portion of the surgical instrument.

US Patent Publication No. 2008-0065082 (Chang) discloses instruments and methods for inserting a rasp into an intervertebral space of a spine and using the rasp to decorticate the adjacent vertebra. More particularly, one embodiment provides an instrument that actively changes the angle of the rasp relative to the instrument. The delivery instrument may use a gear portion to articulate the rasp. A second gear on the rasp may mate with a corresponding gear on the instrument. As the instrument gear rotates relative to the instrument, the instrument gear drives the rasp gear, thereby rotating the rasp to decorticate the vertebra. Trial inserts and methods are also provided to determine an appropriate size of a rasp for decortication.

US Patent Publication No. 2008-0140085 (Gately) discloses a method to insert a spinal implant into a vertebral space, the method including the steps of: grasping the implant with a distal end of an implant insertion tool; holding a proximal end of the implant insertion tool and inserting the implant toward the vertebral space; and manipulating the proximal end to apply a yaw movement to the implant while the implant is attached to the tool and in the vertebral space.

Adjustable TLIF implant inserters are limited in angulation to the axial plane for posterior approach surgeries. These devices do not measure the amount of angulation instilled in the trial. Therefore, there remains a need for adjustable trials that allow for flexion of angles of insertion and measurement of the insertion angle for a lateral trial.

SUMMARY OF THE INVENTION

Several devices and methods are disclosed for inserting lateral trials at trajectories skewed from the intervertebral disc space. Each trial incorporates means to enable controlled angulations into the prepared disc space. These means include bending or pivoting means. Angulations can be performed intra-operatively (on a mayo stand) or in-situ (during or following insertion into the disc). The trial also allows for measurement of the insertion approach/angle to help ensure the implant is inserted at a consistent angle.

Continuously adjustable trials allow for flexible and adaptable angles of approach based upon patient anatomy, surgical preference and numbers of levels to be fused.

DESCRIPTION OF THE FIGURES

FIGS. 7*a*-7*b* disclose angled trials inserted into the disc space via an superior-lateral and inferior-lateral approaches, wherein the trials are angled in the coronal plane.

FIGS. 9*a*-9*d* disclose side views of angled trials wherein the distal head pivots about the sheath in the coronal plane, wherein the trials have varying degrees of angulation.

FIG. 11c discloses a cross-sectional view of the trial of FIG. 11a.

FIGS. 12a-12c disclose perspective views of the second embodiment of a universal trial having a conical range of angulation.

FIGS. 12d-12f disclose side views of the distal end portion of the trial of FIG. 11a set at varying degrees of angulation.

FIG. 13 discloses a cross-sectional view of the universal joint of FIG. 11a, wherein the joint has a tongue-and-groove interface.

DETAILED DESCRIPTION OF THE INVENTION

For the purposes of the present invention, the sum of angles α+β that describe the head/rod orientation always totals 180 degrees. Likewise, the sum of the angles γ+β always totals 180 degrees.

For the purposes of the present invention, "substantially laterally inserting a trial" includes inserting the trial from either the lateral or antero-lateral approach.

Now referring to FIGS. 6-9, there is provided a single-plane adjustment embodiment of the present invention. This embodiment provides variable angular adjustment of the trial head in a single plane.

Figure 1:
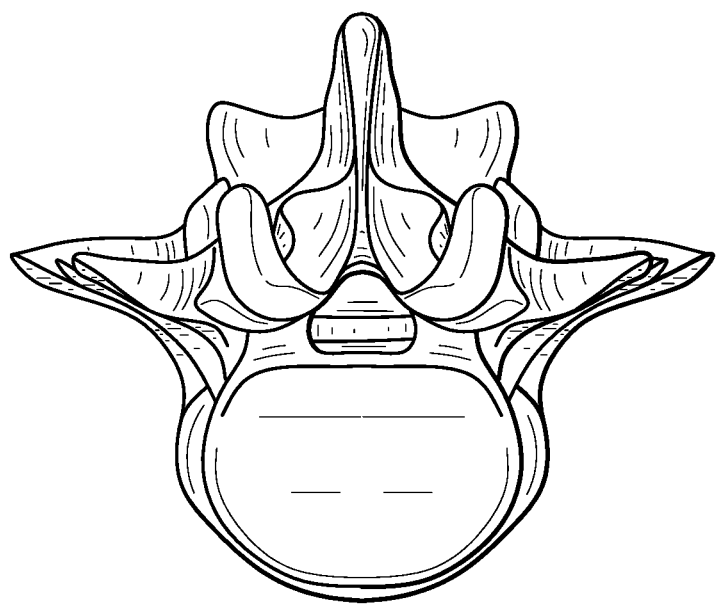
FIG. 1 discloses the conventional paths of direct lateral and anterior-lateral access to a disc space.
Figure 3:
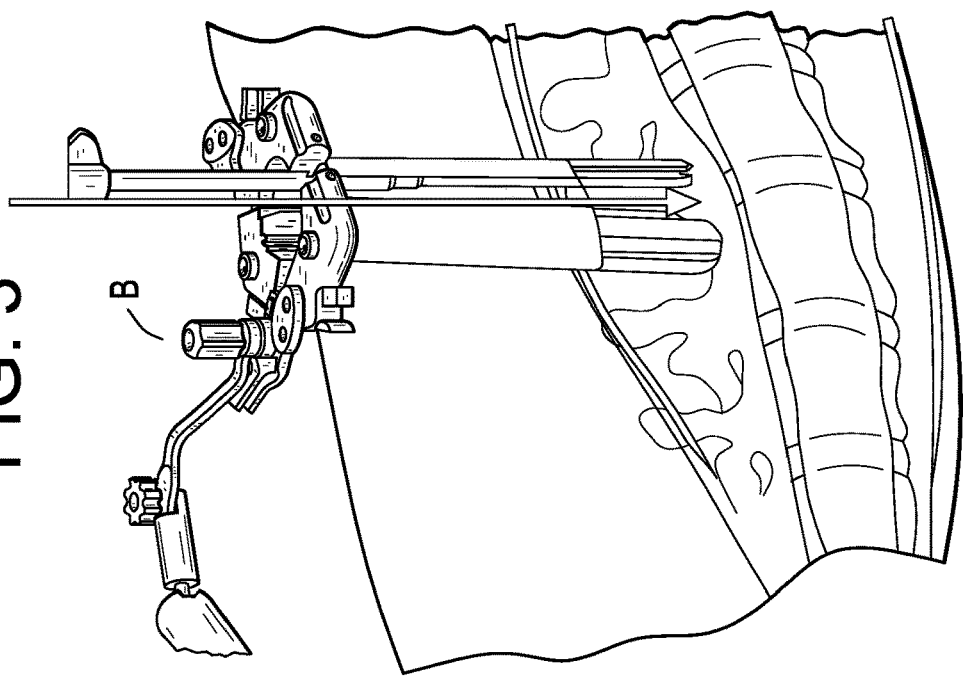
FIGS. 2 and 3 disclose lines of sight for direct lateral access to the disc space, wherein the trajectory is substantially parallel to the disc space.
Figure 2:
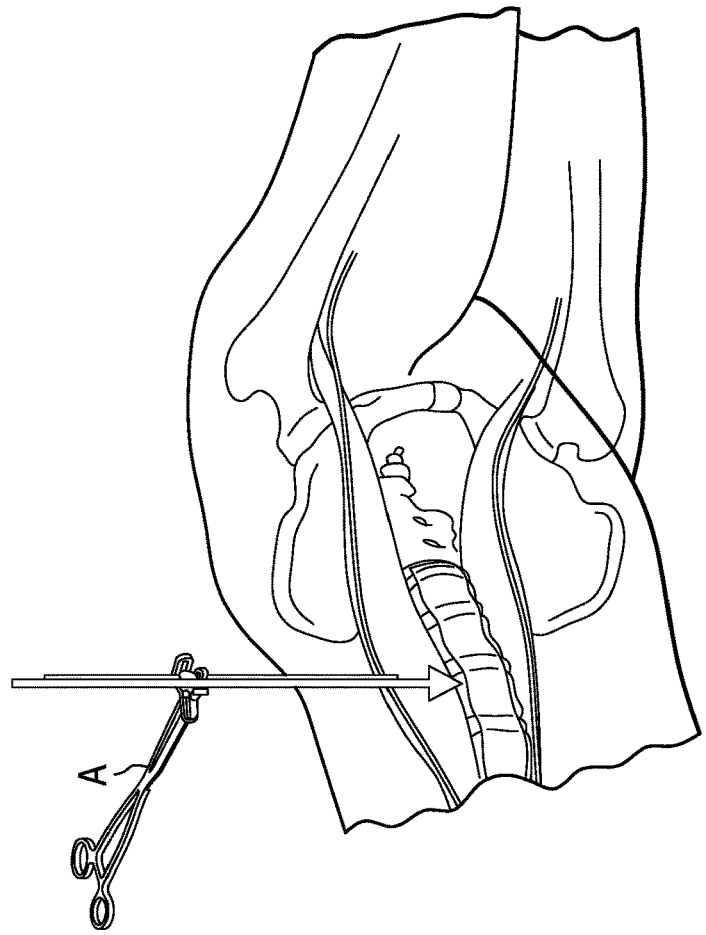
Figure 4B:
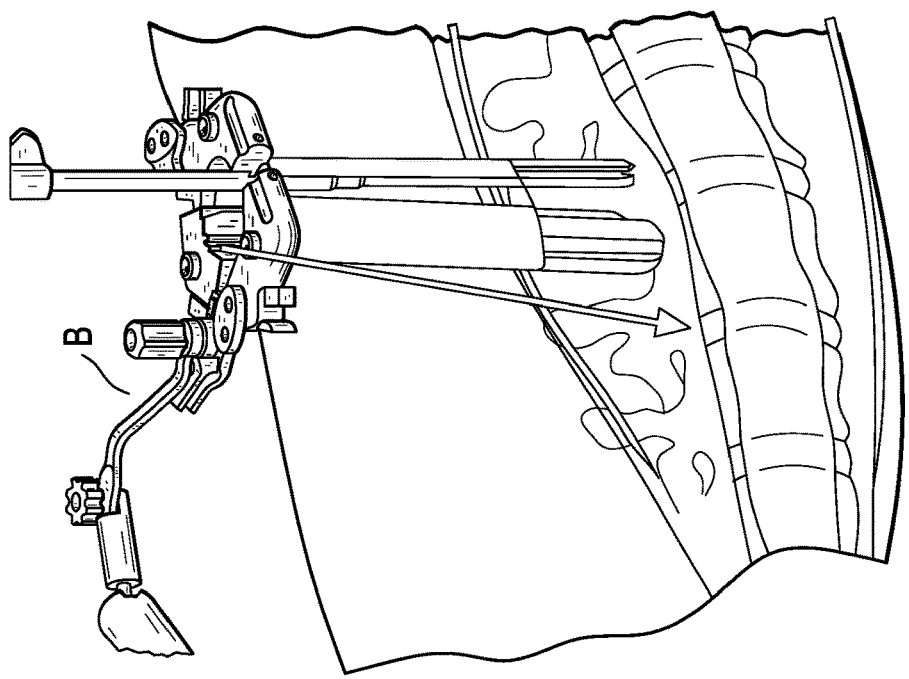
FIGS. 4*a* and 4*b* disclose lines of sight for indirect lateral access to the disc space, wherein the trajectory is substantially skewed with respect to the disc space.
Figure 4A:
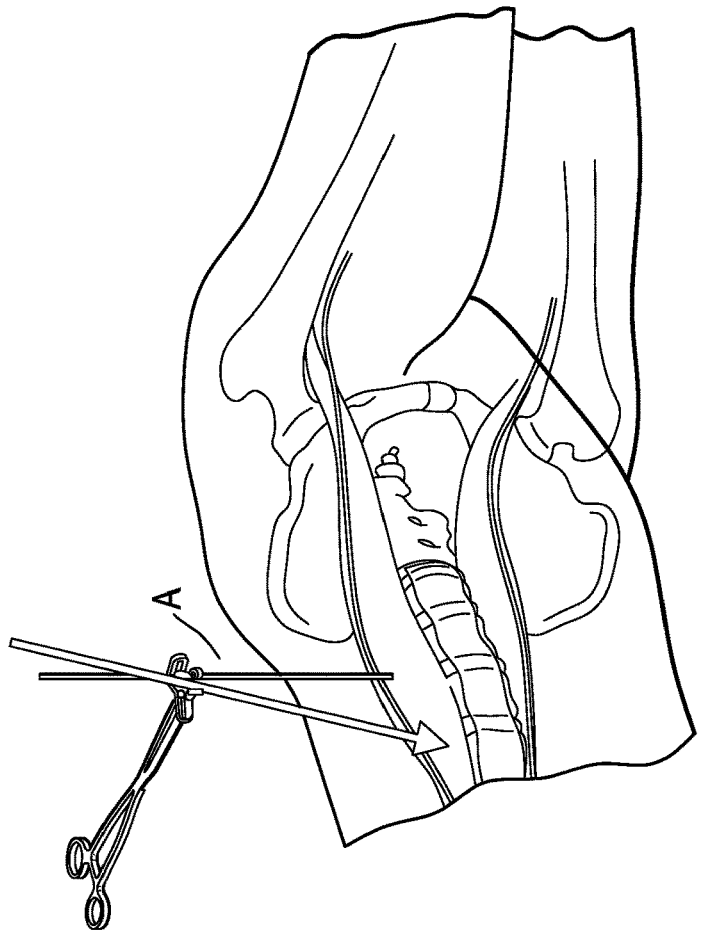
Figure 5:
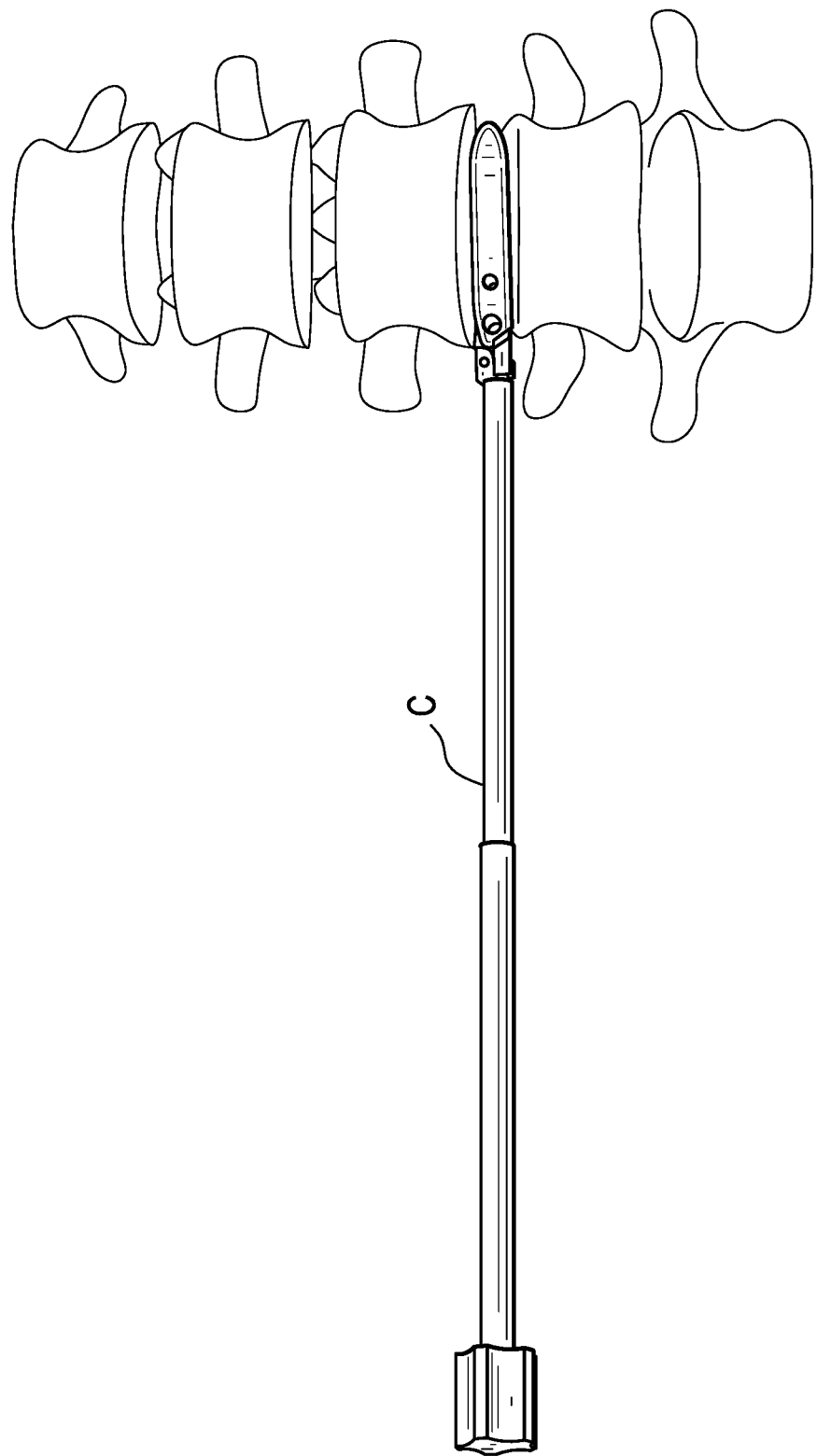
FIG. 5 discloses a trial inserted into the disc space via a straightforward lateral approach.
Figure 6A:
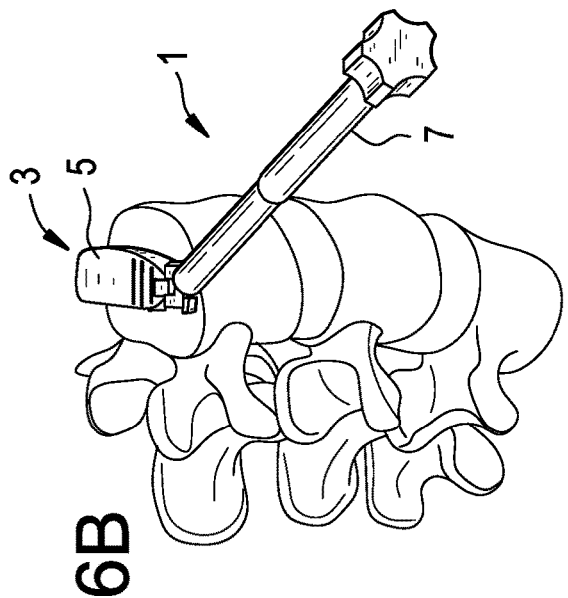
FIGS. 6*a*-6*c* disclose an angled trial inserted into the disc space via an anterior-lateral approach, wherein the trial is angled in the transverse plane.
Figure 6B:
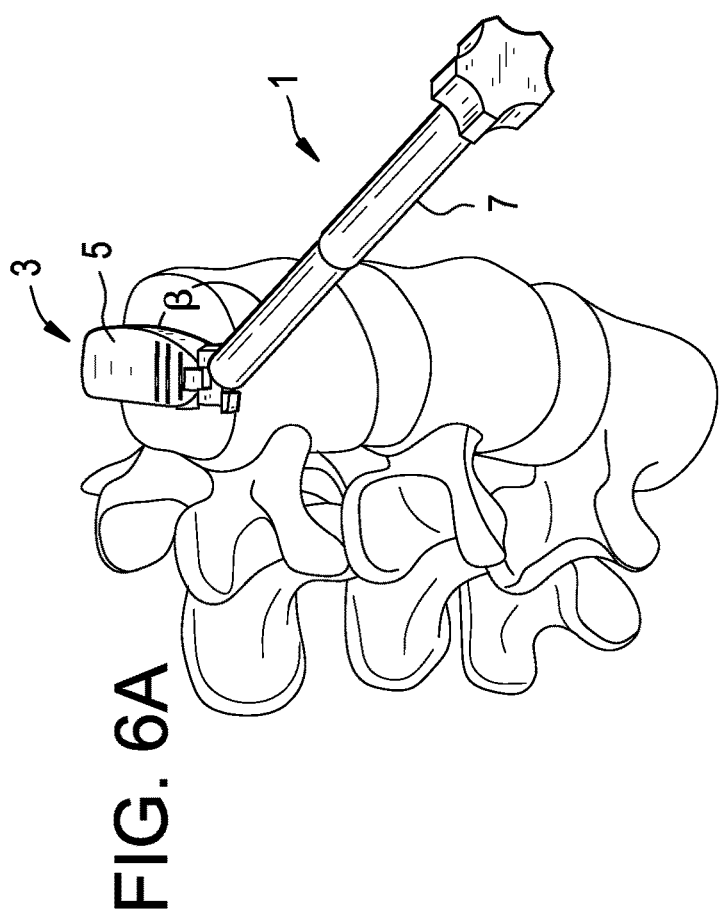
Figure 6C:
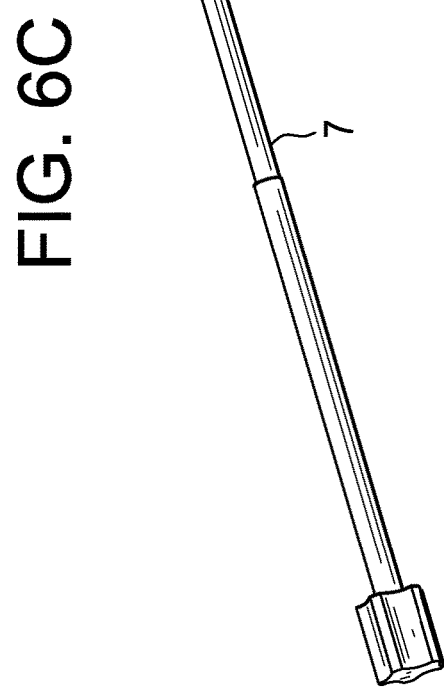
Figure 8A:
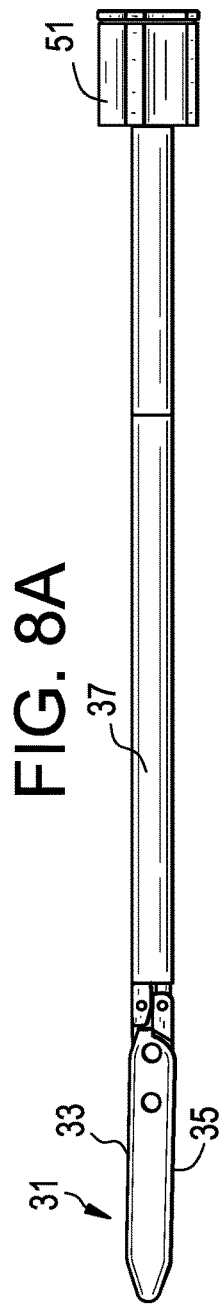
FIGS. 8*a*-8*b* disclose side views of angled trials wherein the distal head pivots about the sheath.
Figure 8B:
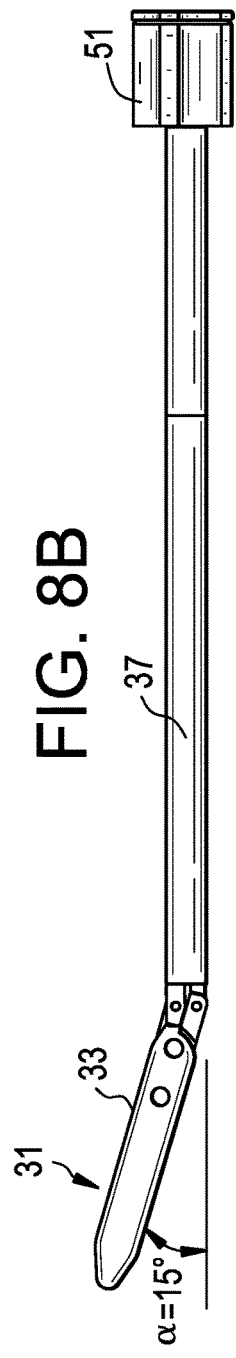
Figure 8C:
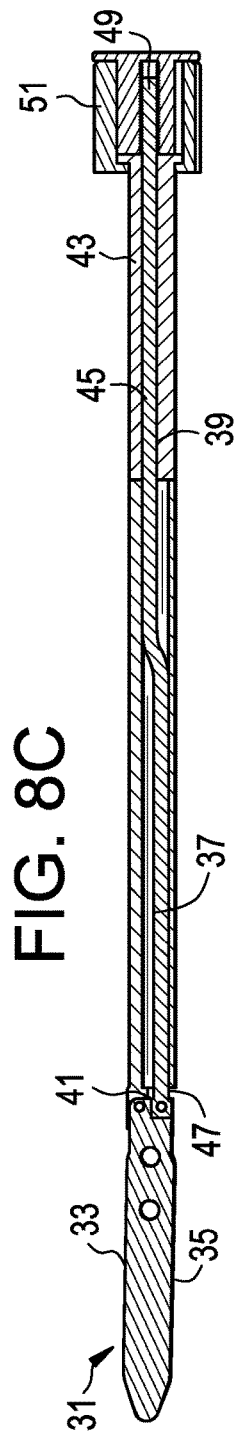
FIG. 8*c* discloses a cross-sectional view of an angled trial wherein the distal head pivots about the sheath.
Figure 8E:
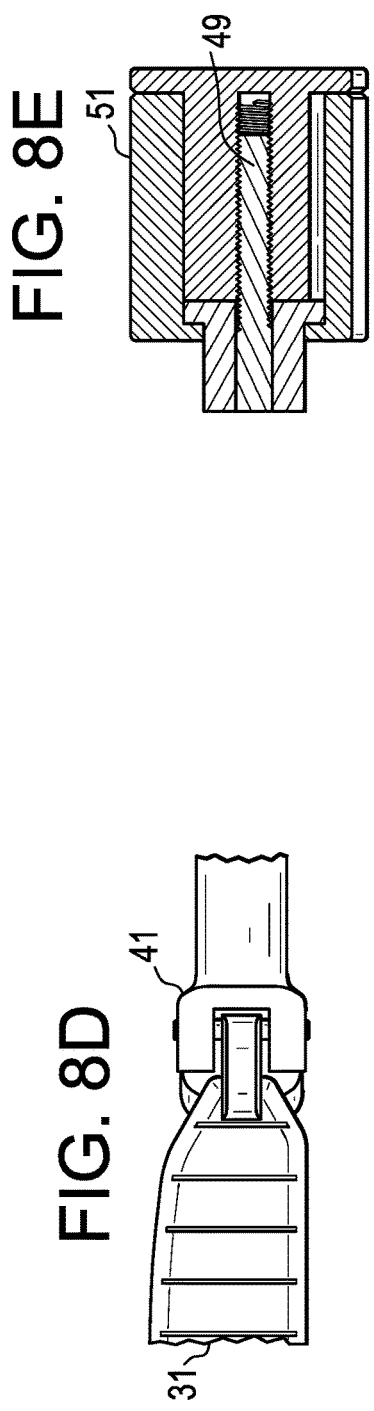
FIG. 8*e* discloses a cross-sectional view of the proximal end portion of the angled trial of FIG. 8*c*.
Figure 8D:
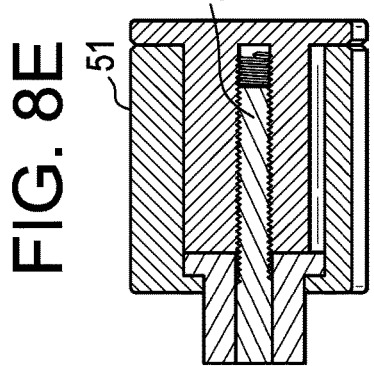
FIG. 8*d* is a side view of the pivoting portion of the trial of FIG. 8*a*.

In some single-plane embodiments, the trial's angulation can be adjusted within a patient's transverse plane. This embodiment is most useful when the trial is inserted upon a transverse plane and in an anterior-lateral approach, as shown in FIGS. 6a-6c. Angulation adjustment in this plane can correct for any deviation of the angle of selected approach from a purely lateral approach to enhance ease of insertion, minimize endplate damage, and determine the angle of approach for implant insertion.

Therefore, and now referring to FIGS. 6a-6c, in accordance with the present invention there is provided a method of trialing an intervertebral disc space, comprising the steps of:
  a) inserting a trial 1 into the disc space, the trial having i) a distal head 3 having an upper surface 5 and a lower surface (not shown), and ii) a proximal rod 7,
  wherein the head and rod form an obtuse angle β when the head is in the disc space, and
  wherein the rod extends substantially parallel to planes defined by the upper surface and the lower surface of the head when the head is in the disc space.

Also in accordance with the present invention, there is provided a method of trialing an intervertebral disc space, comprising the steps of:
  a) creating the disc space,
  b) substantially laterally inserting a trial into the disc space substantially within a transverse plane, the trial having i) a distal head having an upper surface and a lower surface connected by a pair of side walls, the side walls defining planes, and ii) a proximal rod,
  wherein the head and rod form an obtuse angle β in the transverse plane.

In some single-plane embodiments, the trial's angulation can be adjusted along the patient's coronal plane. This embodiment is most useful when the trial is inserted at a coronal angle (preferably a caudal angle) via a direct lateral approach, as shown in FIGS. 7a-b. Angulation adjustment in this plane can correct for any deviation of the angle of selected approach from a purely transverse approach.

FIG. 7a discloses the coronal angle-variable trial inserted superiorly along a direct lateral approach, while FIG. 7b discloses the coronal angle-variable trial inserted inferiorly along a direct lateral approach.

Therefore, now referring to FIGS. 7a-7b, and in accordance with the present invention, there is provided a method of trialing an intervertebral disc space, comprising the steps of :
  a) creating the disc space,
  b) inserting a trial 11 into the disc space, the trial having i) a distal head 13 having an upper surface 15 and a lower surface 17 connected by a pair of side walls 19, the side walls defining a pair of planes, and ii) a proximal rod 21, p1 wherein the head and rod form an obtuse angle γ when the head is in the disc space,
  wherein the rod extends substantially parallel to the pair of planes defined by the side walls of the head when the head is in the disc space.

Also in accordance with the present invention, there is provided a method of trialing an intervertebral disc space, comprising the steps of:
  a) creating the disc space,
  b) inserting a trial 11 into the disc space substantially within a coronal plane, the trial having i) a distal head 13 having an upper surface 15 and a lower surface 17 connected by a pair of side walls 19, the side walls defining a pair of planes, and ii) a proximal rod 21,
  wherein the head and rod form an obtuse angle γ in the coronal plane when the head is in the disc space.

In some preferred embodiments, the adjustment trial that coronally angulates within the coronal plane comprises an internal pusher connected to the trial head via a threaded rod contained within a sheath and controlled by a proximal knob. The range of angles α that are preferred with this trial is between 1 degree and 45 degrees, but more preferably is from 1 degree to 25 degrees. In some preferred embodiments, the knob and rod can have incremental measurement means to either intra-operatively or in-situ record the desired degree of trial angulation. This measurement can provide the surgeon with the desired degree of trial angulation following intradiscal placement of the head. The surgeon thus has the means to insure that the implant is inserted at the same angle as the trial.

Therefore, now referring to FIGS. 8a-8e, in accordance with the present invention there is provided an intervertebral trial for assessing an intervertebral disc space, comprising:
  a) a distal head 31 having an upper surface 33 and a lower surface 35, the surfaces adapted for contacting opposed vertebral endplates;
  b) a sheath 37 having a longitudinal throughbore 39, a distal end portion 41 pivotally connected to the distal head, and a proximal end portion 43;
  c) a rod 45 disposed in the throughbore and having a distal end portion 47 pivotally connected to the distal head and a threaded proximal end portion 49,
  d) a knob 51 abutting the proximal end portion of the sheath and threadably connected to the threaded proximal end portion of the rod,
wherein rotation of the knob moves the rod longitudinally to pivot the distal head about the rod.

Also in accordance with the present invention, there is provided intervertebral trial for assessing an intervertebral disc space, comprising:
  a) a distal head having an upper surface, a lower surface, and a pair of side surfaces connecting the upper and lower surfaces; the pair of side surfaces defining a pair of planes;

b) a sheath having a longitudinal throughbore and having a distal end portion pivotally connected to the distal head, c) a rod disposed in the throughbore and having a distal end portion pivotally connected to the distal head and a proximal end portion, wherein longitudinal movement of the rod pivots the rod between the pair of planes defined by the sidewalls of the distal head.

In some embodiments, and now referring to FIGS. 9a-9d, the knob comprises an outer surface 52 having an indicator 54 that indicates a degree of angulation provided by the trial. In FIGS. 9a-9d, the trials are shown with 0, 5, 10 and 15 degrees of angulation respectively.

Another preferred embodiment of the present invention provides multi-plane or polyaxial angle adjustment, which allows a conical range of angulations between the head and rod. Several embodiments are disclosed below that enable such polyaxial angulations.

In one universal joint embodiment, the universal joint comprises a) a generally spherical ball attached to the trial head, and b) a socket attached to the handle shaft, the socket having a collet that is compressed upon retraction into a sheath and thereby grips the spherical ball to lock the orientation of the trial. In this embodiment, the rod is pulled backward to induce locking of the universal joint.

Figures 10A, 10B, 10C:
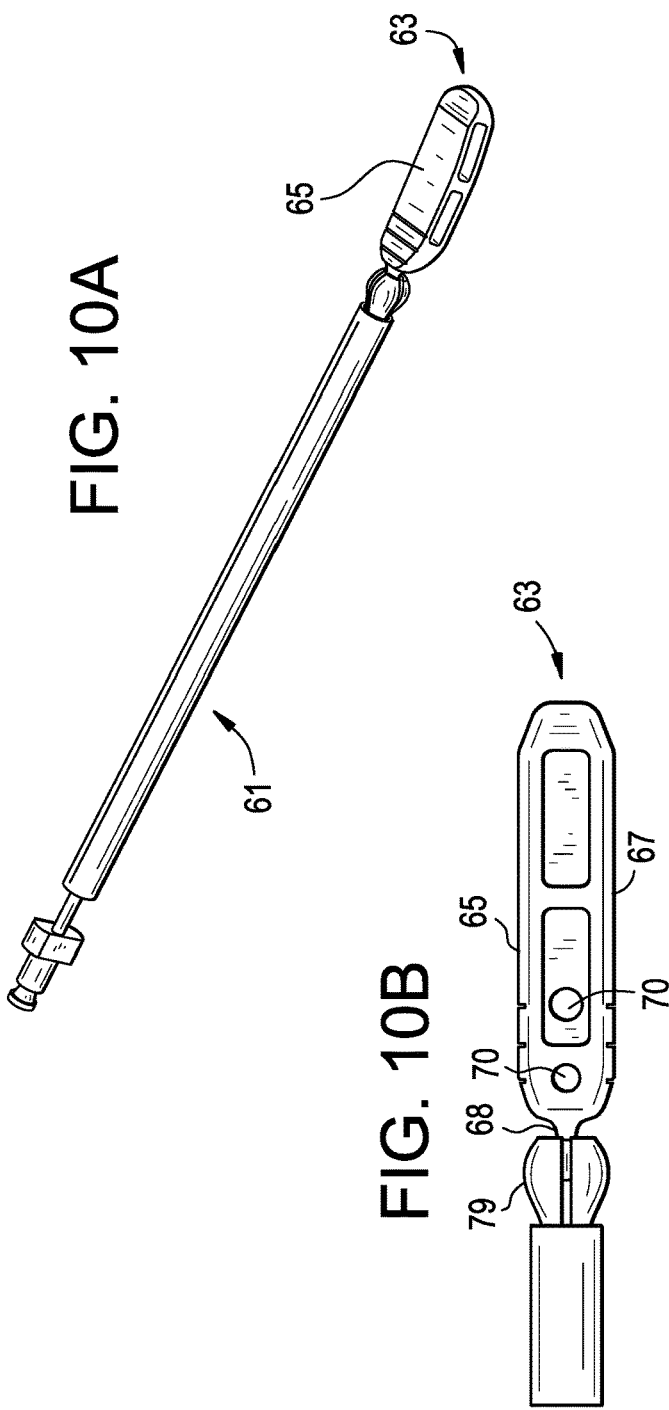
FIG. 10*a* discloses a first embodiment of a universal trial having a conical range of angulation.
FIG. 10*b* discloses a close-up view of the distal end portion of the trial of FIG. 10*a*.
FIG. 10*c* discloses a cross-sectional view of the trial of FIG. 10*a*.
Figure 11A:
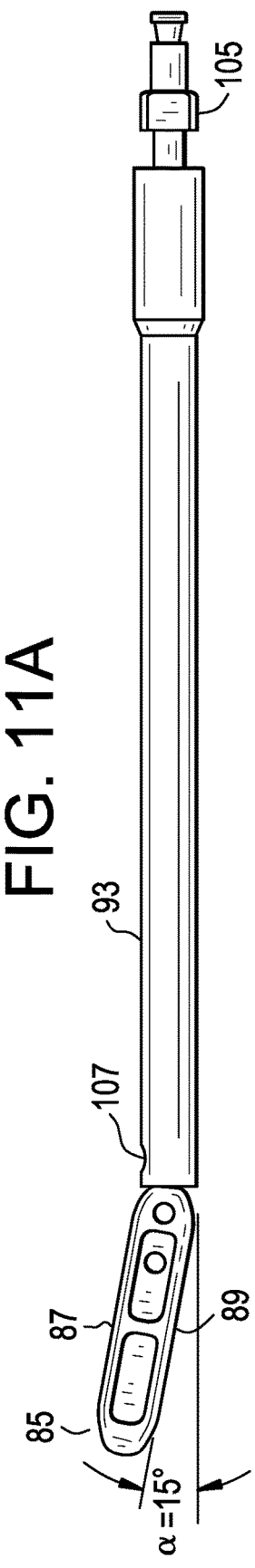
FIG. 11*a* discloses a side view of a second embodiment of a universal trial having a conical range of angulation.
Figure 11B:
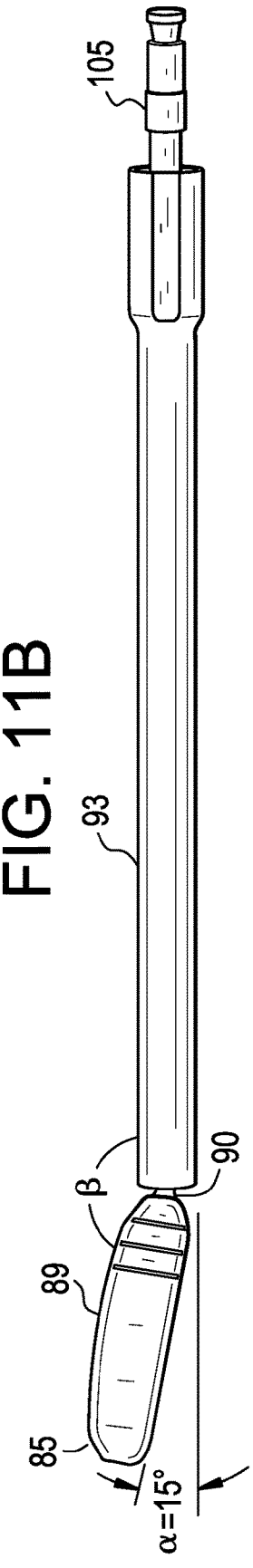
FIG. 11*b* discloses a bottom view of the second embodiment of a universal trial having a conical range of angulation.
Figure 11C:
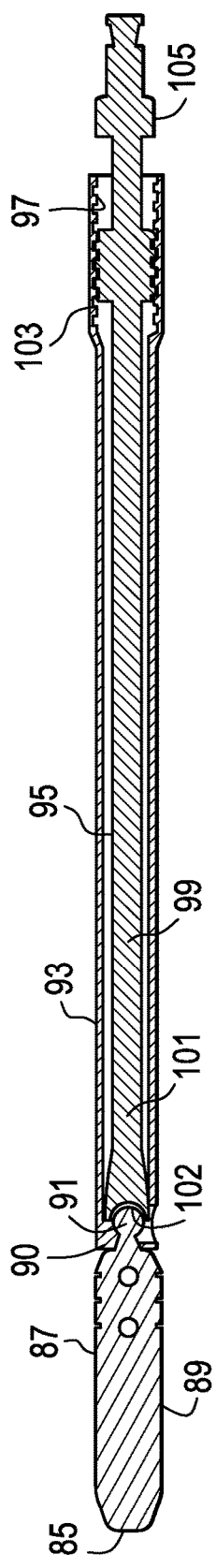

Therefore, now referring to FIGS. 10a and 10b, in accordance with the present invention there is provided an intervertebral trial 61 for assessing an intervertebral disc space, comprising:

a) a distal head 63 having an upper surface 65, a lower surface 67, and a proximal end portion 68 comprising a substantially spherical element 69;

b) a sheath 71 having a throughbore 73 having a proximal end portion 75, c) a rod 77 disposed in the throughbore, the rod having a distal end portion 79 forming a collet, an intermediate portion 81, and a proximal end portion 83, wherein the intermediate portion of the rod mates with the proximal end portion of the throughbore of the sheath, wherein the substantially spherical element of the distal head is rotatably received in the collet to form a universal joint.

Retraction of the rod (or advancement of the sheath) causes the collet to close upon the substantially spherical element, thereby locking a position of the distal head with respect to the rod.

In some embodiments, this polyaxial trial further comprises radiopaque markers 70 provided in the head. These markers assist in radiographically determining the location of the head.

In one universal joint embodiment, and now referring to FIGS. 11a-13, the rod 99 is pushed forward to induce locking of the universal joint. In this embodiment, the universal joint comprises of a) a generally spherical ball 91 attached to a proximal portion of the trial head and b) a poppet 102 having a concavity matching the convexity of the ball, wherein the poppet is formed at the distal end 101 of the rod. The ball is inserted into the throughbore via an open keyway 107 located in the distal end portion of the sheath. To lock the joint at a desired angle, the poppet is advanced to mate with the ball (see FIGS. 12d-f).

Therefore, in accordance with the present invention there is provided an intervertebral trial for assessing an intervertebral disc space, comprising:

a) a distal head 85 having an upper surface 87, a lower surface 89, and a proximal end portion 90 forming a substantially spherical element 91;

b) a sheath 93 having a throughbore 95 having a threaded proximal end portion 97, c) a rod 99 disposed in the throughbore, the rod having a distal end portion 101 forming a poppet 102, a threaded intermediate portion 103, and a proximal end portion 105, wherein the threaded intermediate portion of the rod threadably mates with the threaded proximal end portion of the sheath, wherein the substantially spherical element of the distal head is rotatably received in the poppet to form a universal joint.

Rotation of the threaded rod causes it to advance distally and the poppet to bias against the substantially spherical element, thereby locking a position of the distal head.

In some universal joint embodiments, the sphere and poppet are reversed, so that the proximal end portion of the distal head forms the poppet and the distal end portion of the rod forms a sphere.

Therefore, in accordance with the present invention there is provided an intervertebral trial for assessing an intervertebral disc space, comprising:

a) a distal head having an upper surface, a lower surface, and a proximal end portion forming a joint element; the upper and lower surfaces adapted to contact opposing vertebral endplates;

b) a sheath having a longitudinal throughbore having a proximal end portion and a distal end portion, c) a rod disposed in the throughbore, the rod having a distal end portion rotatably mating with the joint element to form an articulating (e.g., a universal) joint, an intermediate portion, and a proximal end portion, wherein the intermediate portion of the rod is received in the proximal end portion of the throughbore of the sheath, wherein longitudinal distal movement of the rod causes the distal end portion of the rod to bias against the joint element, thereby locking a position of the distal head with respect to the rod.

In some preferred embodiments of the present invention, there is provided an intervertebral trial for assessing an intervertebral disc space, comprising:

a) a distal head having an upper surface, a lower surface, and a proximal end portion comprising a substantially spherical element;

b) a sheath having a throughbore having a threaded proximal end portion, c) a rod disposed in the throughbore, the rod having a distal end portion forming a surface for receiving the substantially spherical element, a threaded intermediate portion, and a proximal handle attachment, wherein the threaded intermediate portion of the rod threadably mates with the threaded proximal end portion of the sheath, wherein the substantially spherical element of the distal head is received in at least the surface of the rod to form a universal joint, wherein rotation of the handle attachment causes the rod to advance and the surface to bias against the substantially spherical element, thereby locking a position of the distal head.

Also in accordance with the present invention, there is provided a method of trialing an intervertebral disc space, comprising the steps of:

a) inserting a trial into the disc space, the trial having i) a distal head having an upper surface and a lower surface connected by a pair of side walls, the side walls defining a first pair of planes, the upper and lower surfaces defining a second pair of planes, and ii) a proximal rod, wherein the head and rod form an obtuse angle when the head is in the disc space, wherein the rod extends through at least one of the first pair of planes defined by the side walls of the head when the head is in the disc space, and wherein the rod extends through at least one of the second pair of planes defined by the upper and lower surfaces of the head when the head is in the disc space, and b) inserting an implant into the disc space.

In some universal joint embodiments, either the distal end of the sheath or the sphere (or both) can have a generally smooth surface to allow for unconstrained adjustment. Alternatively, these components can have features that allow for adjustment to specific desired predetermined angulations. These features can include, but are not limited to undercut, rings, spikes, or teeth. In some incremental adjustment embodiments, and now referring to FIG. 13, the substantially spherical element and the concave lip 111 of the throughbore form a tongue and groove interface comprising tongue 113 and groove 115.

Therefore, in accordance with the present invention, the throughbore of the sheath has a distal end portion forming a concave lip for receiving the substantially spherical element. Also in accordance with the present invention, the substantially spherical element and the concave lip of the throughbore form a tongue-and-groove interface.

In some embodiments, a spring can be incorporated into the pusher shaft or the sheath to enhance the ease of angle adjustment.

Both the single-plane and multi-plane designs of the present invention provide for modular trial heads. The provision of a plurality of heads with a single adjustment handle allows the more costly adjustment handle to be shared across the plurality of heads and so reduces the overall system cost.

In some embodiments, the trial is equipped with an angulation indicator that reports the extent of angulation produced between the head and rod.

Therefore, in accordance with the present invention there is provided a method of trialing an intervertebral disc space, comprising the steps of :
  a) inserting a trial into the disc space, the trial having i) a distal head having an upper surface and a lower surface, ii) a proximal rod, wherein the rod and distal head are pivotally connected, and wherein the head and rod form an obtuse angle when the distal head is in the disc space, and iii) an angulation indicator connected to the rod,
  b) rotating the rod to adjust the obtuse angle, and
  c) reading the angulation indicator on the trial.

In preferred embodiments, there is provided an intervertebral trial for assessing an intervertebral disc space, comprising:
  a) a distal head having an upper surface and a lower surface;
  b) a sheath having a throughbore and having a distal end portion pivotally connected to the distal head,
  c) a rod disposed in the throughbore and having a distal end portion pivotally connected to the distal head and a threaded proximal end portion,
  d) a knob threadably connected to the threaded portion of the rod.
wherein rotation of the knob moves the rod longitudinally to pivot the distal head, and wherein the knob comprises an outer surface having an indicator that indicates a degree of angulation provided by the trial.

Also in accordance with the present invention, there is provided a method comprising the steps of:
  a) laterally inserting a variable-angle trial into an intervertebral disc space,
  b) determining an angle set by the trial in the disc space,
  c) providing the angle to an implant-inserter apparatus,
  d) inserting the implant into the disc space at the angle.

In general, the trials of the present invention are preferably manufactured out of standard biomedical instrument materials, including biocompatible metals such as titanium alloys, cobalt-chrome and stainless steel.

In general, the trials of the present invention may be used in accordance with the implants, instruments and procedures disclosed in:
  a) U.S. Ser. No. 61/385,958, entitled "Multi-Segment Lateral Cages adapted to Flex Substantially in the Coronal Plane", filed Sep. 23, 2010 (DEP6342USPSP);
  b) U.S. Ser. No. 61/410,177, entitled "Multi-Segment Lateral Cages adapted to Flex Substantially in the Coronal Plane", filed Nov. 4, 2010 (DEP6342USPSP1);
  c) U.S. Ser. No. 61/358,220, filed on Jun. 24, 2010, and entitled "Instruments and Methods for Non-Parallel Disc Space Preparation" (DEP6322USPSP), and
  d) U.S. Ser. No. 61/379,194, filed on Sep. 1, 2010, and entitled "Flexible Vertebral Body Shavers" (DEP6323USPSP),
the specifications of which are incorporated by reference in their entireties.

We claim:

1. An intervertebral trial for assessing an intervertebral disc space between opposing upper and lower vertebral endplates, comprising:
  a) a distal head having a flat upper surface, a lower surface, a tapered distal end portion connecting the flat upper surface and lower surface , and a proximal end portion comprising a neck having a longitudinal axis and proximally terminating in a spherical element; wherein the flat upper surface is adapted to contact the upper vertebral endplate and the lower surface is adapted to contact the lower vertebral endplate; and wherein the longitudinal axis of the neck extends between the flat upper surface and lower surface ; wherein the neck has upper and lower surfaces located between the upper and lower surfaces of the distal head;
  b) a sheath having a throughbore,
  c) a rod disposed in the throughbore, the rod having a distal end portion and a proximal end portion, and
  d) an angulation indicator connected to the rod,
  wherein the rod mates with the throughbore of the sheath,
  wherein the spherical element of the distal head is rotatably received in the distal end portion of the rod to form a universal joint, which allows a conical range of angulations between the head and rod,
  wherein the flat upper surface extends linearly from the tapered distal end portion to the proximal end portion,
  wherein the substantially flat upper surface of the distal head is completely distal of the neck, and wherein the substantially flat upper surface is characterized by an absence of fusion-promoting throughholes.

* * * * *